United States Patent
Wozencroft

(10) Patent No.: US 9,242,053 B2
(45) Date of Patent: Jan. 26, 2016

(54) AUTOINJECTION DEVICES

(75) Inventor: Robert Michael Wozencroft, Surrey (GB)

(73) Assignee: OWEN MUMFORD LIMITED, Oxford, Oxfordshire (GB)

( * ) Notice: Subject to any disclaimer, the term of this patent is extended or adjusted under 35 U.S.C. 154(b) by 459 days.

(21) Appl. No.: 13/061,007

(22) PCT Filed: Aug. 28, 2009

(86) PCT No.: PCT/GB2009/051081
§ 371 (c)(1),
(2), (4) Date: Apr. 28, 2011

(87) PCT Pub. No.: WO2010/023481
PCT Pub. Date: Mar. 4, 2010

(65) Prior Publication Data
US 2011/0202011 A1 Aug. 18, 2011

Related U.S. Application Data

(60) Provisional application No. 61/136,340, filed on Aug. 28, 2008.

(30) Foreign Application Priority Data

Aug. 28, 2008 (GB) .................................. 0815653.1

(51) Int. Cl.
| | |
|---|---|
| *A61M 5/315* | (2006.01) |
| *A61M 5/50* | (2006.01) |
| *A61M 5/20* | (2006.01) |
| *A61M 5/46* | (2006.01) |
| *A61M 5/24* | (2006.01) |

(52) U.S. Cl.
CPC ........... *A61M 5/5013* (2013.01); *A61M 5/2033* (2013.01); *A61M 5/315* (2013.01);
(Continued)

(58) Field of Classification Search
CPC ... A61M 5/315; A61M 5/5013; A61M 5/142; A61M 5/46; A61M 5/20
USPC .................. 604/198, 191–192, 207, 240, 110
See application file for complete search history.

(56) References Cited

U.S. PATENT DOCUMENTS

| 2,876,770 | A | * | 3/1959 | White | ................... | A61M 5/326 |
|---|---|---|---|---|---|---|
| | | | | | | 604/198 |
| 4,273,123 | A | * | 6/1981 | Lemelson | ........... | A61M 5/3213 |
| | | | | | | 604/110 |

(Continued)

FOREIGN PATENT DOCUMENTS

| DE | 102005038933 A1 | 2/2007 |
|---|---|---|
| DE | 202007000578 U1 | 3/2007 |

(Continued)

OTHER PUBLICATIONS

British Search Report, dated Dec. 22, 2008, from corresponding British application.

(Continued)

*Primary Examiner* — Rebecca E Eisenberg
*Assistant Examiner* — Matthew A Engel
(74) *Attorney, Agent, or Firm* — Young & Thompson

(57) ABSTRACT

An autoinjection device has front and rear separable assemblies (10) and (12). The rear assembly contains a drive assembly which is triggered or unlatched by rearward movement of an actuating sleeve (14) extending from the front assembly. A locking dial (16) is provided which locks the actuating sleeve against rearward movement until the dial is moved to an unlocked position. The dial automatically returns to a locked position upon initial rearward movement of the actuating member (14), so that, when the actuating member (14) moves forwardly after completion of an injection, it locks out to shroud the needle of the autoinjection device. The docking dial can be made integral with the actuating member (14) in an alternative embodiment.

22 Claims, 14 Drawing Sheets

(52) U.S. Cl.
CPC ....... *A61M5/31505* (2013.01); *A61M 5/31511* (2013.01); *A61M 5/46* (2013.01); *A61M 5/24* (2013.01); *A61M 2005/206* (2013.01); *A61M 2005/2013* (2013.01); *A61M 2005/2073* (2013.01); *A61M 2005/2407* (2013.01); *A61M 2005/2488* (2013.01)

(56) References Cited

U.S. PATENT DOCUMENTS

| | | | | |
|---|---|---|---|---|
| 4,617,012 | A * | 10/1986 | Vaillancourt | A61M 39/10 285/12 |
| 4,725,267 | A * | 2/1988 | Vaillancourt | A61M 5/3202 604/192 |
| 4,747,831 | A * | 5/1988 | Kulli | A61M 5/322 604/110 |
| 4,795,432 | A * | 1/1989 | Karczmer | A61M 5/3257 604/110 |
| 4,887,998 | A * | 12/1989 | Martin | A61B 5/1438 604/110 |
| 4,927,416 | A * | 5/1990 | Tomkiel | A61M 5/315 604/198 |
| 4,935,016 | A * | 6/1990 | Deleo | A61M 5/3271 604/198 |
| 4,998,924 | A * | 3/1991 | Ranford | A61M 5/3271 604/110 |
| 5,059,185 | A * | 10/1991 | Ryan | A61M 5/3243 600/576 |
| 5,080,648 | A * | 1/1992 | D'Antonio | A61M 5/2425 604/135 |
| 5,104,380 | A * | 4/1992 | Holman | A61M 5/20 604/117 |
| 5,156,599 | A * | 10/1992 | Ranford | A61M 5/3271 128/919 |
| 5,271,744 | A * | 12/1993 | Kramer | A61M 5/1723 604/135 |
| 5,295,963 | A * | 3/1994 | Deeks | A61M 5/3257 604/110 |
| 5,300,030 | A * | 4/1994 | Crossman | A61M 5/2033 604/134 |
| 5,312,370 | A * | 5/1994 | Talonn | A61M 5/3271 604/197 |
| 5,338,310 | A * | 8/1994 | Lewandowski | A61B 5/1438 604/110 |
| 5,599,309 | A * | 2/1997 | Marshall | A61M 5/2033 604/117 |
| 5,601,536 | A * | 2/1997 | Crawford | A61M 25/0618 604/166.01 |
| 5,609,577 | A * | 3/1997 | Haber | A61M 5/3243 604/110 |
| 5,674,203 | A * | 10/1997 | Lewandowski | A61B 5/1438 128/919 |
| 5,735,823 | A * | 4/1998 | Berger | A61M 5/3243 604/192 |
| 5,746,727 | A * | 5/1998 | Graves | A61M 25/0631 604/198 |
| 5,795,336 | A * | 8/1998 | Romano | A61M 5/3271 604/110 |
| 5,879,337 | A * | 3/1999 | Kuracina | A61M 5/3243 604/192 |
| 5,928,205 | A * | 7/1999 | Marshall | A61M 5/24 604/192 |
| 6,099,503 | A * | 8/2000 | Stradella | A61M 5/2033 604/131 |
| 6,203,530 | B1 * | 3/2001 | Stewart, Sr. | A61M 5/2033 604/207 |
| 6,221,044 | B1 | 4/2001 | Greco | |
| 6,287,278 | B1 * | 9/2001 | Woehr | A61M 25/0618 604/110 |
| 6,302,868 | B1 * | 10/2001 | Mohammad | A61B 5/1438 604/192 |
| 6,623,458 | B2 * | 9/2003 | Woehr | A61M 5/3273 128/919 |
| 6,629,959 | B2 * | 10/2003 | Kuracina | A61B 5/1411 604/192 |
| 6,679,864 | B2 * | 1/2004 | Gagnieux | A61M 5/326 604/110 |
| 6,749,588 | B1 * | 6/2004 | Howell | A61M 5/3273 604/110 |
| 6,776,775 | B1 * | 8/2004 | Mohammad | A61M 5/322 604/195 |
| 6,860,871 | B2 * | 3/2005 | Kuracina | A61B 5/1411 604/192 |
| 6,971,516 | B2 * | 12/2005 | Hansen | A61B 19/0262 206/366 |
| 7,004,930 | B2 * | 2/2006 | Marshall | A61M 5/46 604/198 |
| 7,066,907 | B2 * | 6/2006 | Crossman | A61M 5/2033 604/110 |
| 7,112,187 | B2 * | 9/2006 | Karlsson | A61M 5/20 604/187 |
| 7,229,432 | B2 * | 6/2007 | Marshall | A61M 5/326 604/110 |
| 7,361,160 | B2 * | 4/2008 | Hommann | A61M 5/2033 604/198 |
| 7,632,243 | B2 * | 12/2009 | Bialecki | A61M 25/0618 604/110 |
| D623,732 | S * | 9/2010 | Brady | D24/113 |
| 7,811,261 | B2 * | 10/2010 | Rubinstein | A61M 5/326 604/198 |
| 7,927,314 | B2 * | 4/2011 | Kuracina | A61B 5/150572 604/110 |
| 8,162,882 | B2 * | 4/2012 | Rubinstein | A61M 5/326 604/110 |
| RE43,473 | E * | 6/2012 | Newby | A61B 5/1438 604/110 |
| 8,409,149 | B2 * | 4/2013 | Hommann | A61M 5/2033 604/198 |
| 2003/0078546 | A1 * | 4/2003 | Jensen | A61M 5/3202 604/232 |
| 2005/0203466 | A1 * | 9/2005 | Hommann | A61M 5/2033 604/240 |
| 2005/0277893 | A1 * | 12/2005 | Liversidge | A61M 5/31501 604/198 |
| 2006/0089593 | A1 * | 4/2006 | Landau | A61M 5/30 604/68 |
| 2006/0224124 | A1 * | 10/2006 | Scherer | A61M 5/2033 604/220 |
| 2007/0027430 | A1 * | 2/2007 | Hommann | A61M 5/2033 604/207 |
| 2008/0215001 | A1 * | 9/2008 | Cowe | A61M 5/326 604/110 |
| 2008/0262443 | A1 * | 10/2008 | Hommann | A61M 5/2033 604/264 |
| 2009/0124981 | A1 * | 5/2009 | Evans | A61M 5/2033 604/197 |
| 2009/0227950 | A1 * | 9/2009 | Jensen | A61M 5/326 604/110 |
| 2010/0042053 | A1 * | 2/2010 | Dillard, III | A61M 5/3257 604/198 |
| 2010/0069845 | A1 * | 3/2010 | Marshall | A61M 5/20 604/135 |
| 2011/0077599 | A1 * | 3/2011 | Wozencroft | A61M 5/2033 604/192 |
| 2011/0202011 | A1 * | 8/2011 | Wozencroft | A61M 5/2033 604/192 |
| 2011/0202080 | A1 * | 8/2011 | Nicholls | A61B 5/1411 606/182 |
| 2012/0010641 | A1 * | 1/2012 | Nicholls | A61B 5/15186 606/182 |
| 2012/0289930 | A1 * | 11/2012 | Rubinstein | A61M 5/326 604/506 |
| 2012/0296276 | A1 * | 11/2012 | Nicholls | A61M 5/31501 604/110 |

FOREIGN PATENT DOCUMENTS

| | | |
|---|---|---|
| GB | 2443606 A | 5/2008 |
| JP | H11503637 A | 3/1999 |
| JP | 2005177503 A | 7/2005 |
| JP | 2006500150 A | 1/2006 |
| JP | 2008521482 A | 6/2008 |
| WO | 9413342 A1 | 6/1994 |
| WO | 0247746 A1 | 6/2002 |

(56) References Cited

FOREIGN PATENT DOCUMENTS

| | | | |
|---|---|---|---|
| WO | 2004028598 A1 | | 4/2004 |
| WO | WO 2004/028598 | * | 4/2004 |
| WO | 2004098687 A1 | | 11/2004 |
| WO | 2007036676 A1 | | 4/2007 |
| WO | 2007051331 A1 | | 5/2007 |

OTHER PUBLICATIONS

International Search Report, dated Dec. 1, 2009, from corresponding ISR application.

Translation of Japanese Office Action, dated Sep. 3, 2013, from corresponding JP application.

* cited by examiner

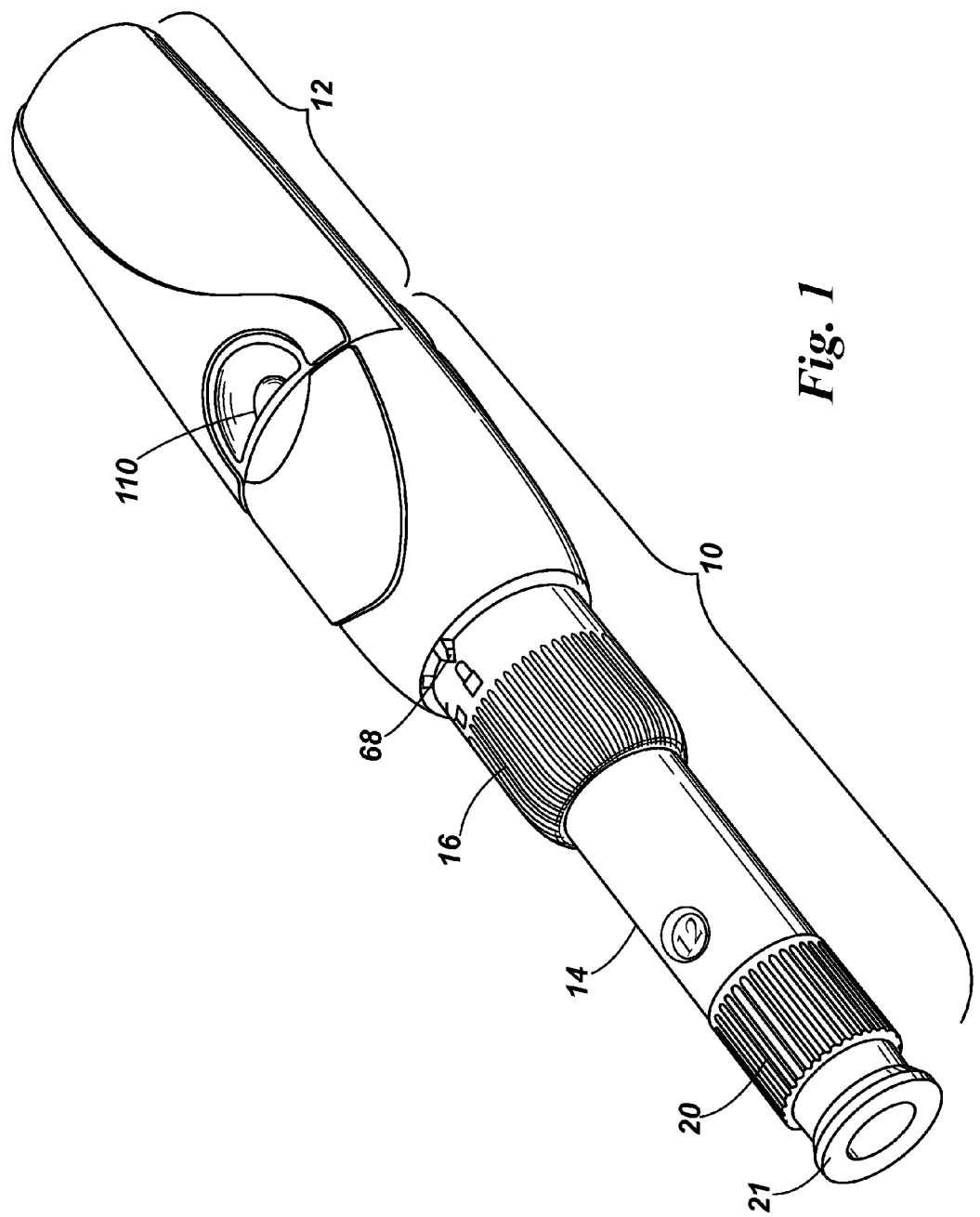

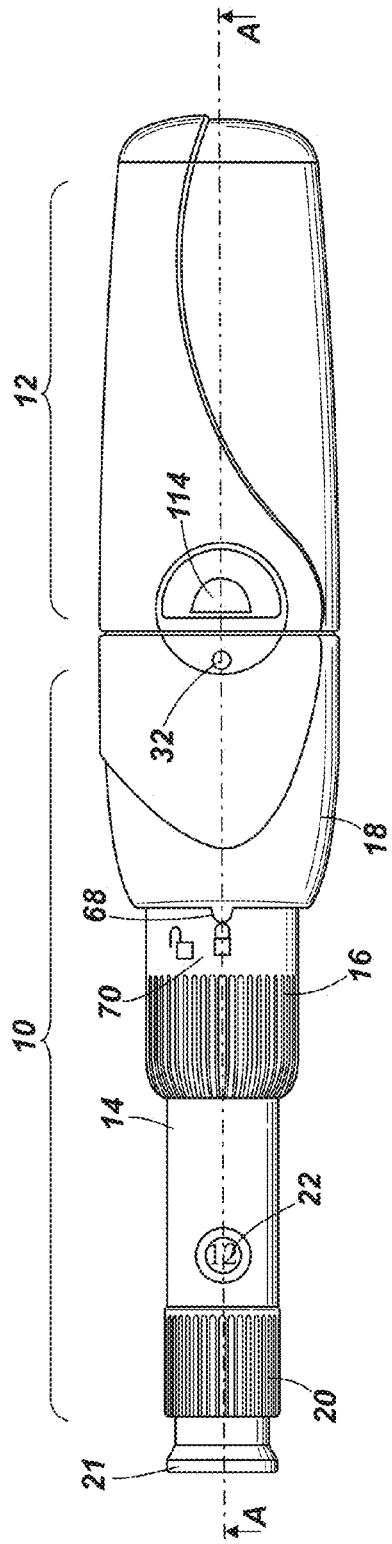
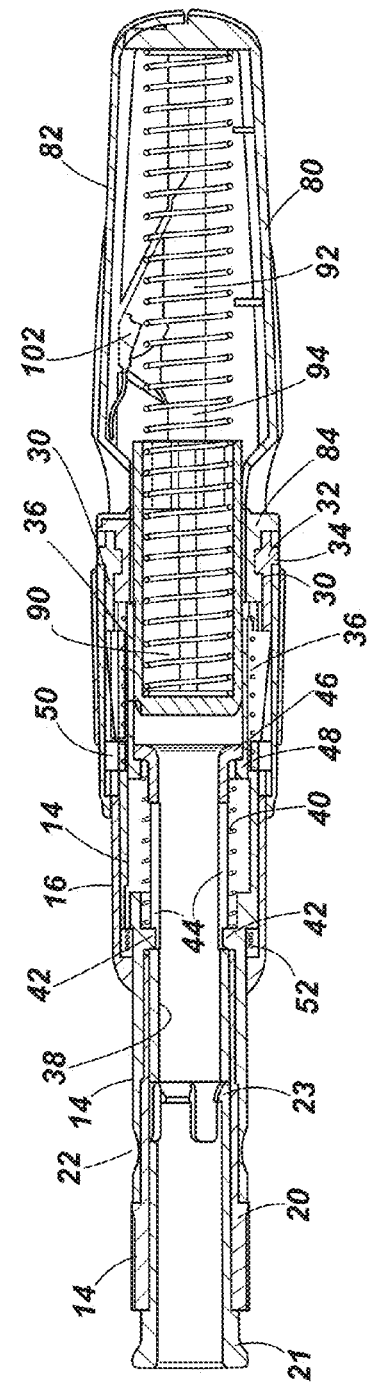
Fig. 2(a)
Fig. 2(b)

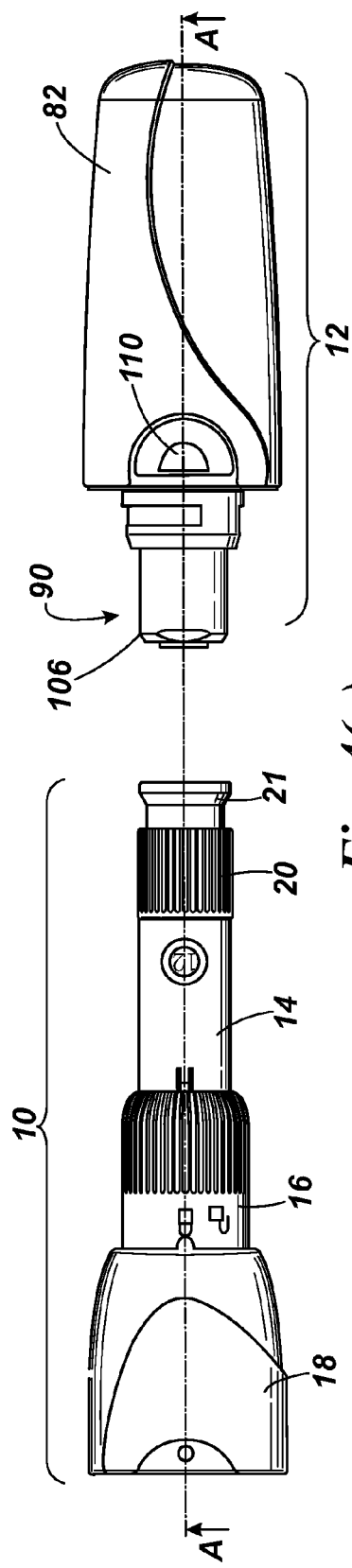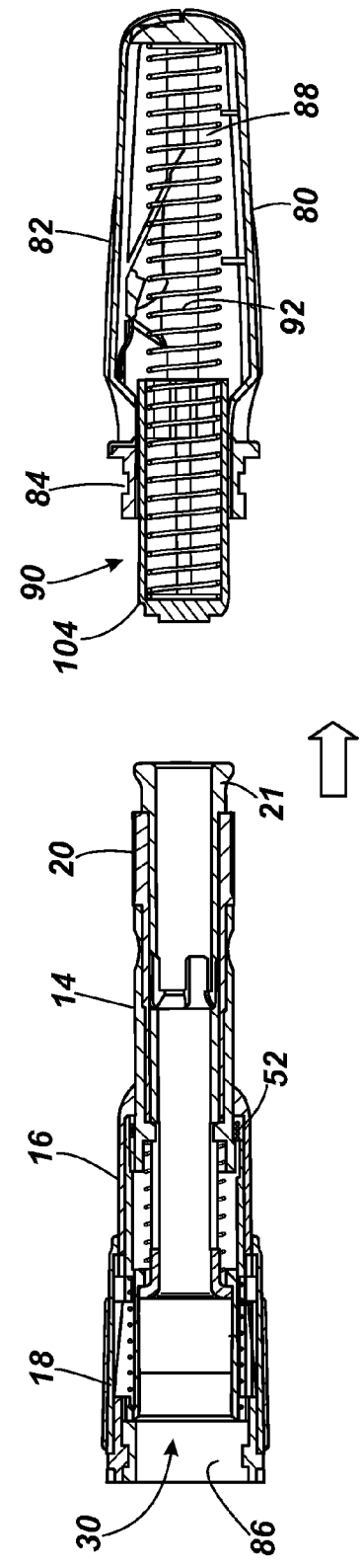
Fig. 4(a)
Fig. 4(b)

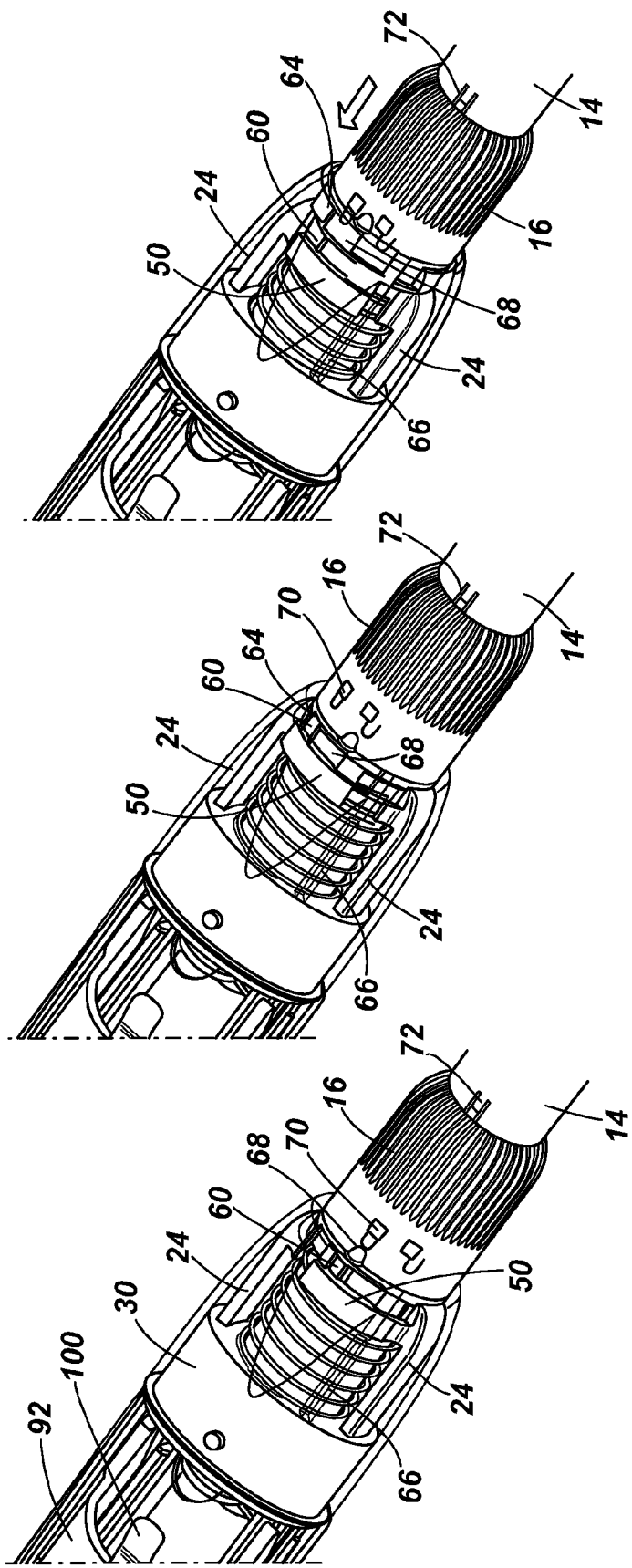

AUTOINJECTION DEVICES

This invention relates to autoinjection devices and, in particular, but not exclusively, to reusable autoinjection devices.

There is an increasing demand for autoinjection devices to be reusable. Because in such devices some form of partial disassembly is usually required in order to allow a spent syringe to be replaced by a fresh one, it is particularly important to ensure that there is some form of safety measure to ensure that, when the injector is reassembled and the drive mechanism is re-primed, there is a reliable safety lock or the like to ensure that the device is left safe and can only be fired following release of the safety lock.

Accordingly, in one aspect, this invention provides an autoinjection device, comprising:

a main body;

a drive mechanism in said main body for being fired to expel a dose from a syringe in use;

an actuating member associated with said main body and moveable from a first position to a second position in which said mechanism is fired;

a locking member associated with said actuating member for preventing said actuating member reaching said second position, the locking member and the actuating member being relatively moveable between locked and unlocked positions when said actuating member is in said first position, wherein on moving said locking member to its unlocked position, and after moving said actuating member to its second position, return of said actuating member to its first position is accompanied by return of said locking member to its locked position.

In preferred embodiments therefore the locking member resets to its locking position when the actuating member returns to its first, rest position.

The locking member may be a separate component moveably mounted with respect to the actuating member and the main body, or it may be associated with or form an integral part of the body.

Preferably, the actuating member is biased towards its first position, and the locking member may conveniently be biased towards its locked position. In preferred arrangements therefore the locking member is moved to its unlocked position and the actuating member moved against its bias to fire the drive mechanism. Release of the load on the actuating member returns it to its first position whereupon the bias on the locking member resets it to its locked position.

Although other arrangements are possible, it is preferred for the actuating member to be linearly moveable between the first and second positions.

Preferably, said actuating member includes a needle shroud portion and, upon completion of said injection, return of said actuating member to its first position shrouds the needle of the syringe with said shroud portion. In this manner the actuating member serves a dual purpose both to fire the drive mechanism but also to shroud the needle. Furthermore, in the described embodiment, since the locking member returns to the locked position as the actuating member returns to its first position, the arrangement provides an effective lockout for the shroud portion.

Although other arrangements are possible, the locking member is preferably angularly moveable between the locked and unlocked positions.

A number of different arrangements are possible to allow the locking member to prevent the actuating member from reaching the second position, in one particularly preferred arrangement, the locking member is capable of limited angular movement with respect to the actuating member but longitudinally fixed with respect thereto, and the locking member and the housing have cooperating abutment surfaces that are rotated out of blocking alignment when the locking member is moved to the unlocked position.

In a preferred embodiment, one of the actuating member and said locking member have spaced recesses provided therein, corresponding to the locking and unlocked positions, and the other thereof has a toothed element capable of unidirectional angular movement from the locked to the unlocked recess when the actuating member is in its first position, movement of the actuating member towards said second position axially withdrawing the toothed element from the unlocked recess whereupon it is allowed to return to be in angular registration with the locking recess.

The drive mechanism may take many forms but in a preferred in embodiment includes a drive spring, a drive member longitudinally moveable within said housing, and a latch for latching the drive member in a primed position, wherein said actuating member is operable to release to said latch.

Preferably, said latch includes at least one side portion extending generally parallel to the axis of the drive spring and having an inclined surface adapted to cooperate with a respective complementary inclined surface on said actuating member to release said latch, when said actuating member moves towards its second position. In order to provide symmetrical loading, the latch preferably includes two side portions with there being two respective inclined surfaces on the actuating member.

The main body is conveniently formed of separable forward and rearward parts, with the rearward part containing at least a major portion of the drive mechanism and the forward part supporting said actuating member and said locking member. Preferably, the actuating member extends forwardly of said main body, generally to surround the needle and to contact the injection site in use. The actuating member may include a moveable adjustable portion associated therewith for adjusting the effective length of said actuating member and therefore the penetration depth of the syringe needle in use.

In another aspect, this invention provides an autoinjection device comprising a main body having separable forward and rearward parts, the rearward part containing a drive mechanism operated by a latch, and the forward part of said main body having an actuating member extending forwardly of the body and adapted to be driven rearwardly into the body to release said latch when applied to an injection site and pressed.

In another aspect this invention provides an autoinjection device comprising front and rear separable rear housing portions, the rear housing portion containing a drive mechanism including a drive energy store, a drive member and a latch arrangement to latch the drive member in a primed position for being unlatched for forward movement, the forward housing portion including an actuating member having a needle shroud sleeve portion extending forwardly of the housing portion, the actuating member being moveable rearwardly to unlatch the drive member, and a syringe carrier mounted on or in said actuating member for longitudinal movement with respect thereto.

Whilst the invention has been described above, it extends to any inventive combination of the features set out above, or on the following description or claims.

The invention may be performed in various ways, and an embodiment thereof will now be described by way of example only, reference being made to the accompanying drawings in which:

FIG. 1 is a general perspective view of an autoinjector in accordance with this invention;

FIGS. 2(a) and (b) are side and longitudinal views respectively of the autoinjector of FIG. 1 in a rest position;

FIG. 3 is a perspective view of the autoinjector in a rest position with the outer case separated for clarity;

FIGS. 4(a) and (b) are side and longitudinal views respectively illustrating the priming operation;

FIGS. 5(a) and (b) are side and longitudinal views respectively of the autoinjector primed and with a pre-filled syringe loaded;

FIGS. 6(a), (b) and (c) are longitudinal section, transverse section and side views respectively on the autoinjector unlocked and ready to inject;

FIGS. 7(a), (b) and (c) are respective detailed views on the locking mechanism, showing it in the locked position, the unlocked position and the reset position respectively;

FIGS. 8(a) and (b) are side and longitudinal views respectively showing activation of the injection;

FIG. 9 is a view of the autoinjector with the outer case separated for clarity, at the activation stage;

FIGS. 10(a) and (b) are respective side and longitudinal sections views when the injection is complete but with the device still pressed against the skin;

FIGS. 11(a) and (b) are respective side and longitudinal section showing the autoinjector device following withdrawal from the injection site;

Figure 3:
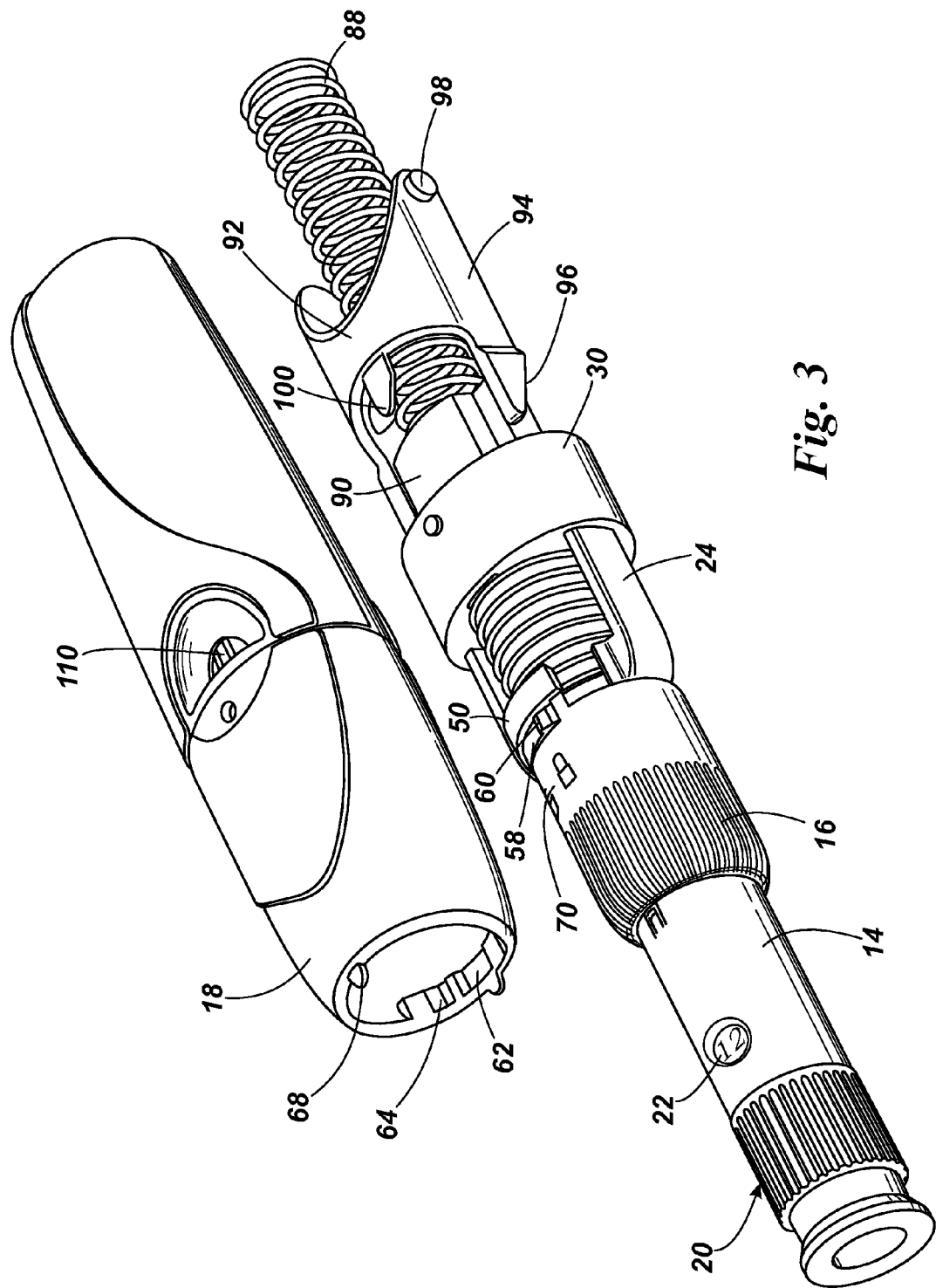

Referring initially to FIG. 1, the illustrated embodiment of autoinjector comprises separable front and rear assemblies 10, 12 respectively. As will be evident below, the front and rear assemblies are connected by a bayonet type fitting to allow easy insertion and withdrawal of a syringe containing medicament. The rear assembly comprises a drive mechanism to be described in more detail below, and the forward assembly includes an actuating member, or longitudinal moveable sleeve 14, the forward portion of which is visible in FIG. 1; and a locking member, or rotary locking dial 16.

Referring now in more detail to FIGS. 2, 3, 12 and 13, the front assembly 10 comprises a front case 18 through which projects the sleeve 14 and the forward portion of the dial 16. Threadedly received in the front end of the sleeve is a depth adjuster 20 having marked thereon penetration depth indicia that are visible through a window 22 in the sleeve. The rear end of the sleeve has twin aft extending prongs 24 each having a ramp surface 26. The prongs 26 pass rearwardly through slots 28 in a collar 30, the collar being secured in the front case by means of diametrically opposed pips 32 that seat in diametrically opposed recesses 34 on the front case 18. The sleeve 14 is biased forwardly by means of a spring 36 acting between the collar 30 and the sleeve 14. A syringe carrier 38 is slideably received within the forward end of the sleeve 14 and biased rearwardly by a carrier spring 40. Axial movement of the syringe carrier 38 within the sleeve 14 is limited by means of two inwardly directed lugs 42 that run in slots 44 in the syringe carrier 38. The out-turned rearward end 46 of the syringe carrier 38 cooperates with an internally facing rib 48 on a forward cylindrical extension of the collar 30.

Figure 12:
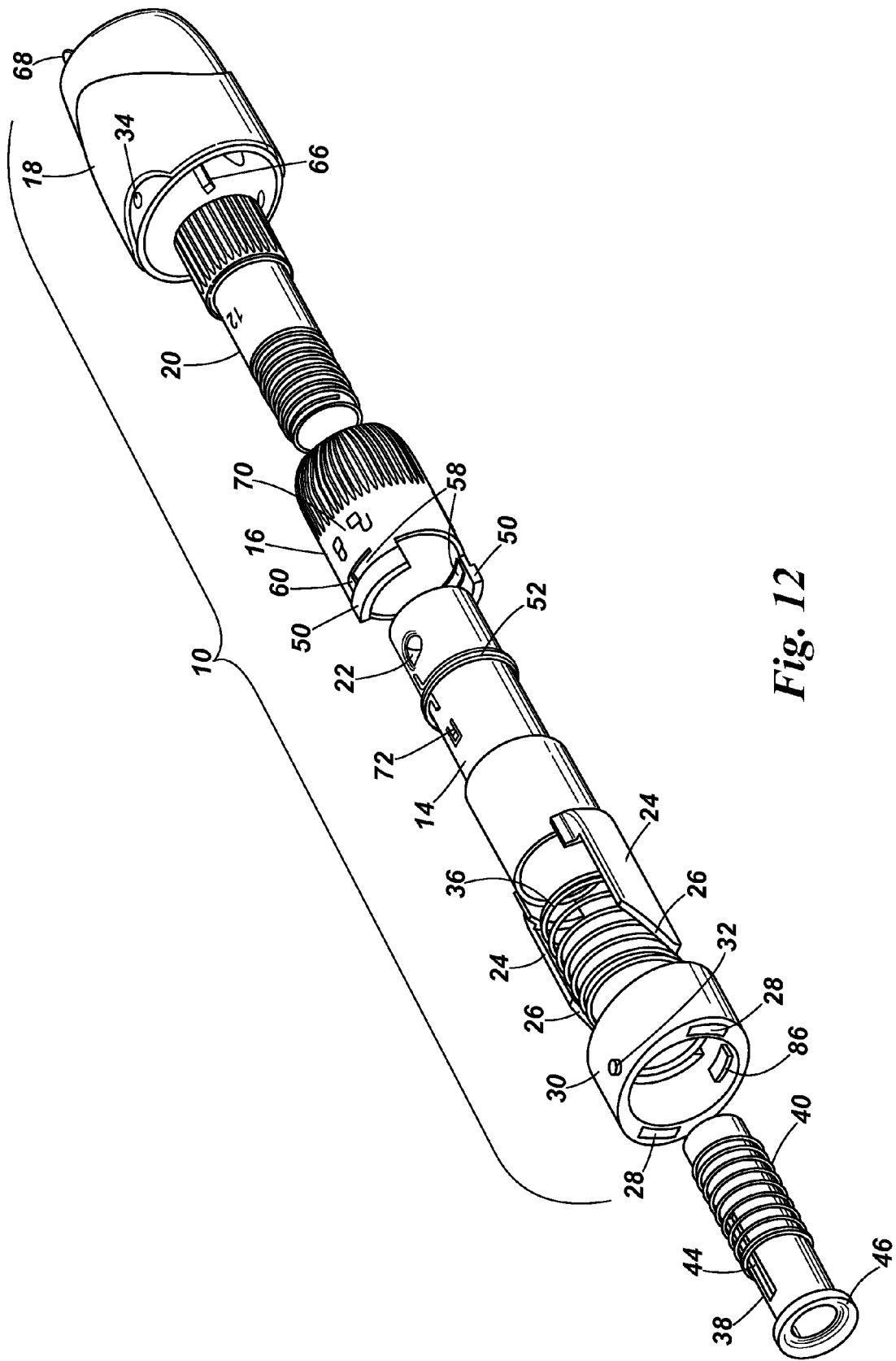
FIG. 12 is an exploded view of the front assembly.

As seen in FIG. 3, the locking dial has two diametrically opposed part-cylindrical rearward extensions 50 which upstand radially from the outer surface of the dial 16. Immediately forward of this are two sprung tongues 58, each having an externally facing tooth 60 at the free, clockwise end as viewed from the front. A torsion spring 52 acts between the sleeve 14 and the dial 16 to bias the dial in a counter-clockwise direction as viewed from the front. When the assembly is in the at rest position, the teeth 60 are received in corresponding 'locked' recesses 62 on the inside of the front cover 18 but the resilience of the tongues means that the teeth 60 can be clicked into respective 'unlocked' recesses 64 by rotating the dial against the bias of the torsion spring 52. Referring particularly to FIG. 12, the inside wall of the front case 18 has two diametrically opposed upstanding webs 66, which cooperate with the extensions 50 on the dial 16 selectively to allow or prevent rearward movement of the dial 16 within the front case 18, dependent on whether the dial is in an unlocked position (teeth 60 in 'unlocked' recesses 64) or a locked position (teeth 60 in 'locked' recesses 62). The front case has a pointer 68 which cooperates with indicia 70 on the dial 16 to indicate whether the dial is locked or unlocked. The dial 16 is rotatable on the front end of the sleeve 14, but the two move longitudinally together as the dial 16 is clipped onto the front end of the sleeve by means of an outwardly facing sprung tooth 72.

The dial 16 and the sleeve 14 are urged forwardly by the spring 36 so that, at rest, the tooth 60 is urged forwardly into engagement with the 'locked' recess 62. However, when the device has been unlocked, with the tooth then in recess 64, rearward movement of the sleeve and dial as the injector device is pressed against the skin moves the tooth 60 out of the 'unlocked' recess 64 axially, so that, under the influence of the torsion spring 52, the dial then rotates back part way towards the position in which the teeth 60 are axially aligned with the 'locked' recesses 62, put held short of exact alignment by the webs 66.

Figure 13:
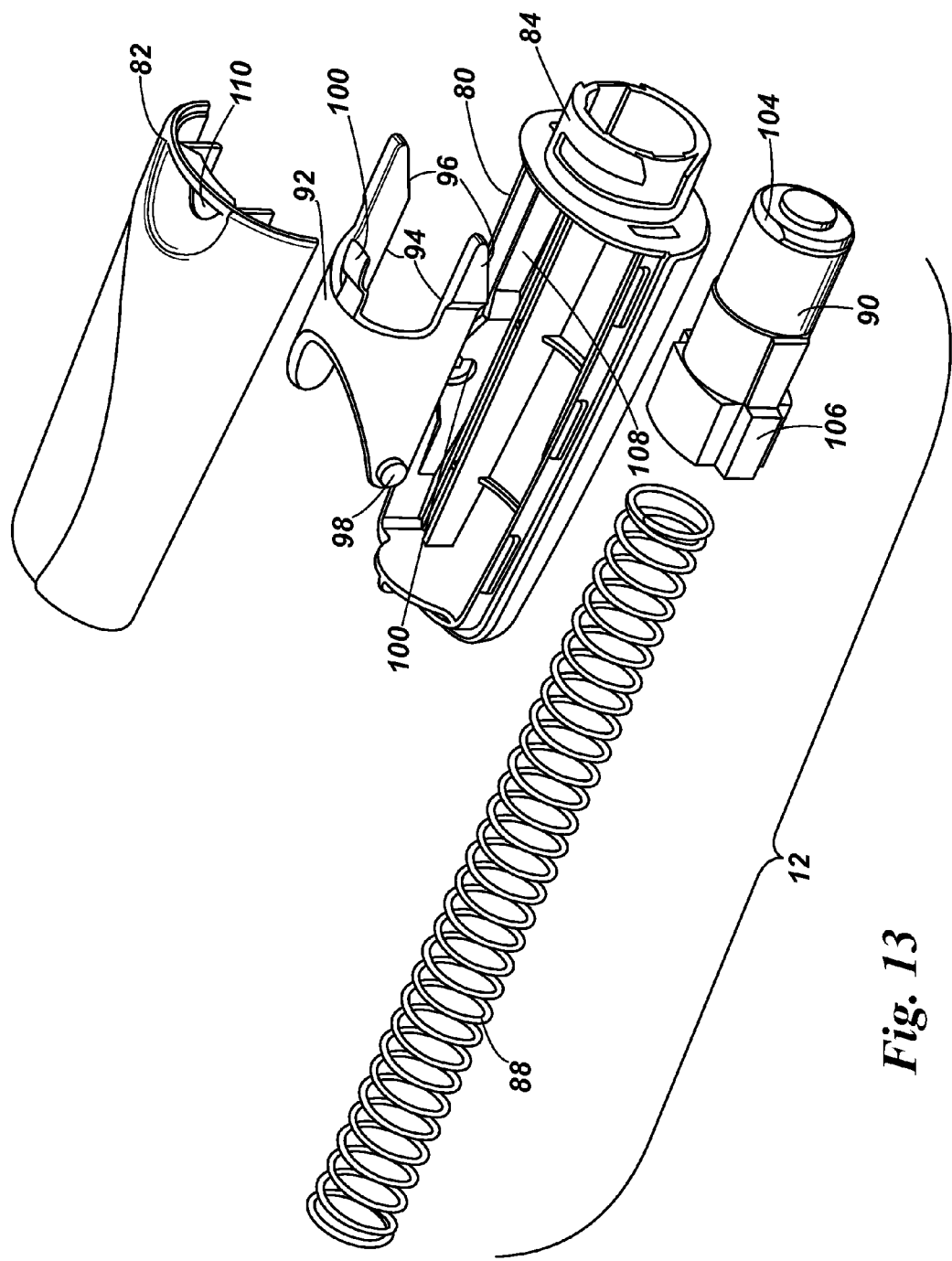
FIG. 13 is an exploded view of the rear assembly.

Turning now to the rear housing assembly 12, and particularly to FIGS. 3 and 13, the rear assembly 12 comprises an outer casing formed by a case bottom 80 onto which is snap-fitted a case top 82. The forward end of the case bottom 80 is formed with a bayonet fitting 84 that cooperates with a complementary fitting 86 provided on the inside of the collar 30 forming part of the front assembly 10. Located in the casing is the main drive spring 88 fitting within a hollow tubular piston 90. A latch 92 of saddle form has forwardly extending arms 94 having ramp surfaces 96 designed to cooperate with the ramp surfaces 26 on the arms 24 of the sleeve 14 in the front assembly 10. Rearward extensions of the arms 94 are provided with pivot lugs 98 which are received in seats 100 in the case bottom to allow the latch 92 to pivot. Extending forwardly of the central portion of the latch 92 is a leaf spring 100 which acts on the case top 82 to bias the latch downwardly to a latching position. To the rear of the leaf spring, on the underside of the latch is a latch abutment 102. The piston 90 has a latch surface 104 on its front end that cooperates with the latch abutment 102 to latch the piston in its primed position. The piston 90 also has lateral stub guides 106 that run in guide grooves 108 in the case bottom 80 to guide the piston and prevent its rotation. The piston is formed of a plastics material of a distinctive colour such as red and the case top 82 has an injection complete window 110 through which the piston is visible when in a forward position to indicate injection complete.

Figure 5A:
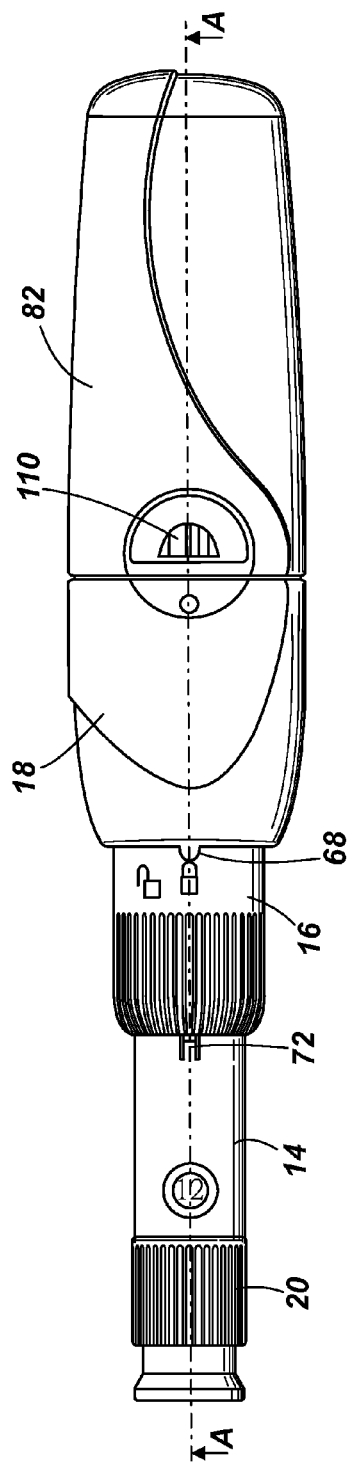
Figure 5B:
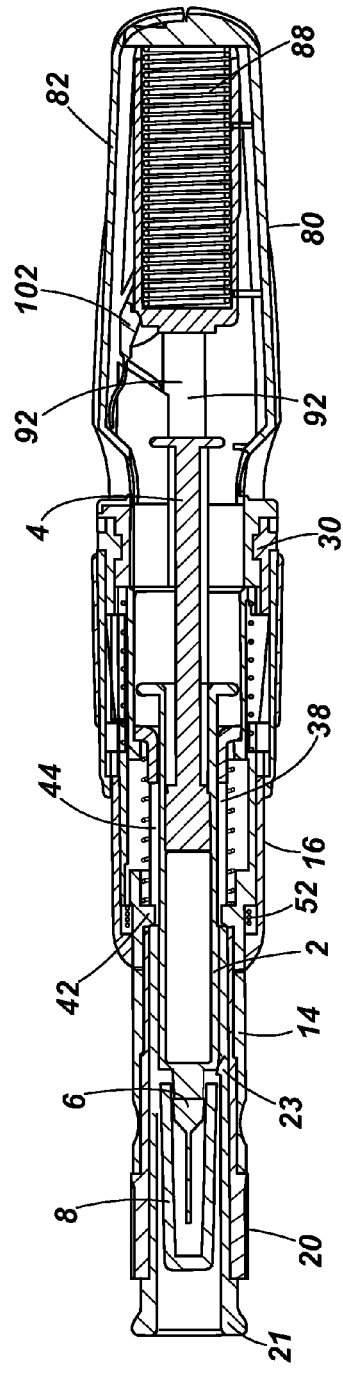

Turning now to operation of the device, assuming that it is in the at rest position shown in FIGS. 2(a) and (b), the rear assembly 12 is firstly uncoupled from the front assembly 10 and inverted so that a needle cap remover 21 located in the end of the depth adjuster faces the piston 90. The front assembly and rear assembly are pushed together so that the piston 90 is pushed by the needle cap remover against the bias of the main drive spring 88 until the piston is latched by the latch abutment 102 engaging the latch surface 104 on the piston (see FIGS. 4(*a*) and (*b*)). A syringe comprising a barrel 2, a plunger 4, a needle 6 and a needle cap 8 is loaded into the front assembly 10 by inserting the syringe into the syringe carrier 38 and pushing until the needle cap passes a tooth 23 on the rear end of the needle cap remover 21 (see FIG. 5(*b*)). The front and rear assemblies 10, 12 are then assembled together by connecting the bayonet coupling 84, 86.

Figure 6C:
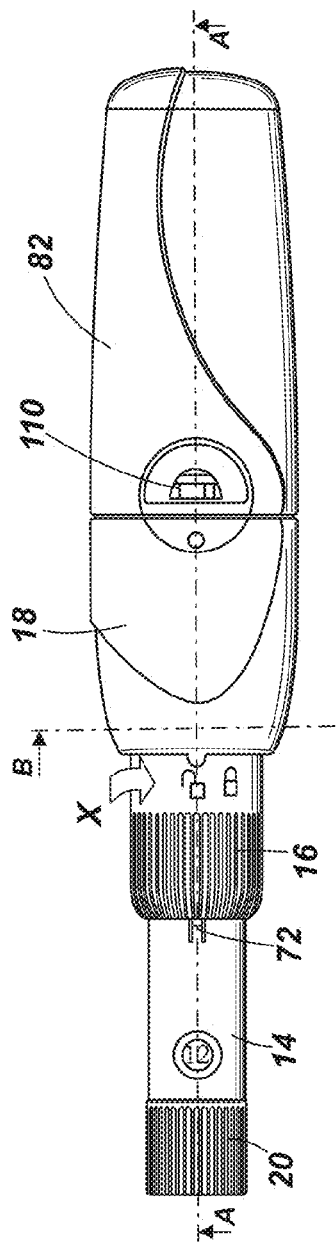
Figure 6A:
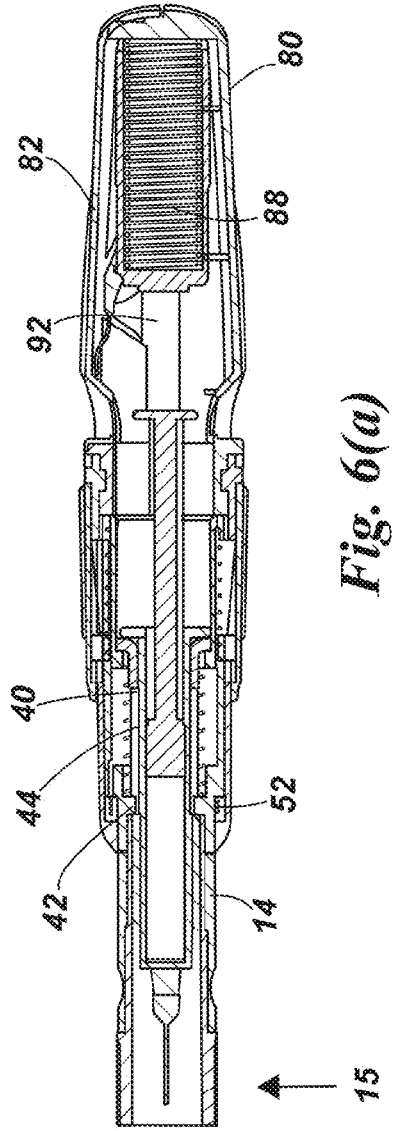
Figure 6B:
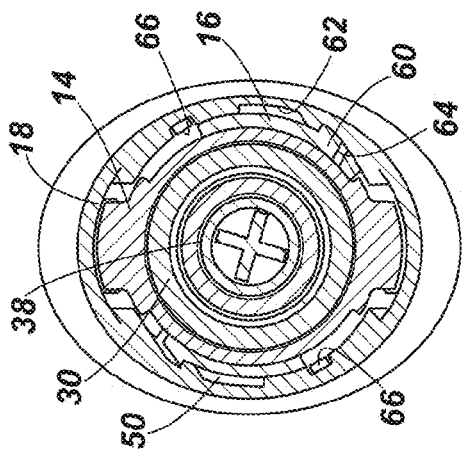
Figure 8A:
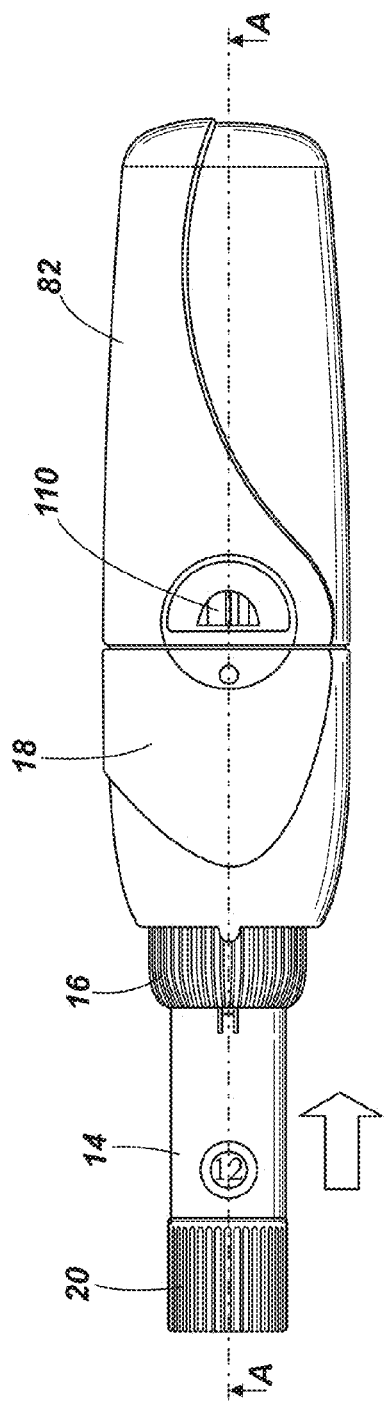
Figure 8B:
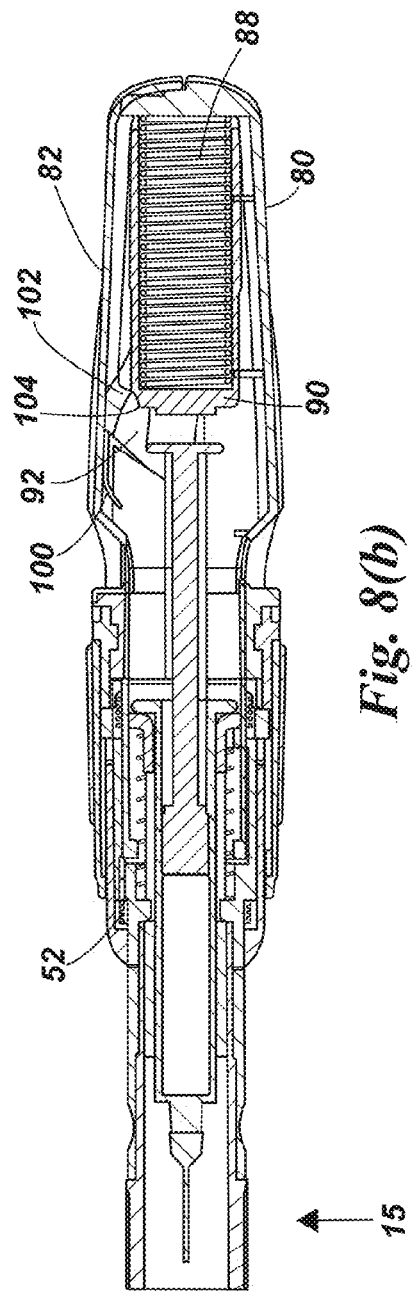

The device is then unlocked by rotating the locking dial 16 in the direction of arrow X in FIG. 6(*c*) against the bias of the torsion spring 52. This action rotates the extensions 50 on the rotary dial 16 out of axial alignment with the web 66 on the inside of the front housing 18 (see FIGS. 7(*a*) and (*b*)). At the same time the tooth 60 on the locking dial 16 moves from the 'locked' recess 62 to the 'unlocked' recess 64 against the bias of the torsion spring 52.

Figure 9:
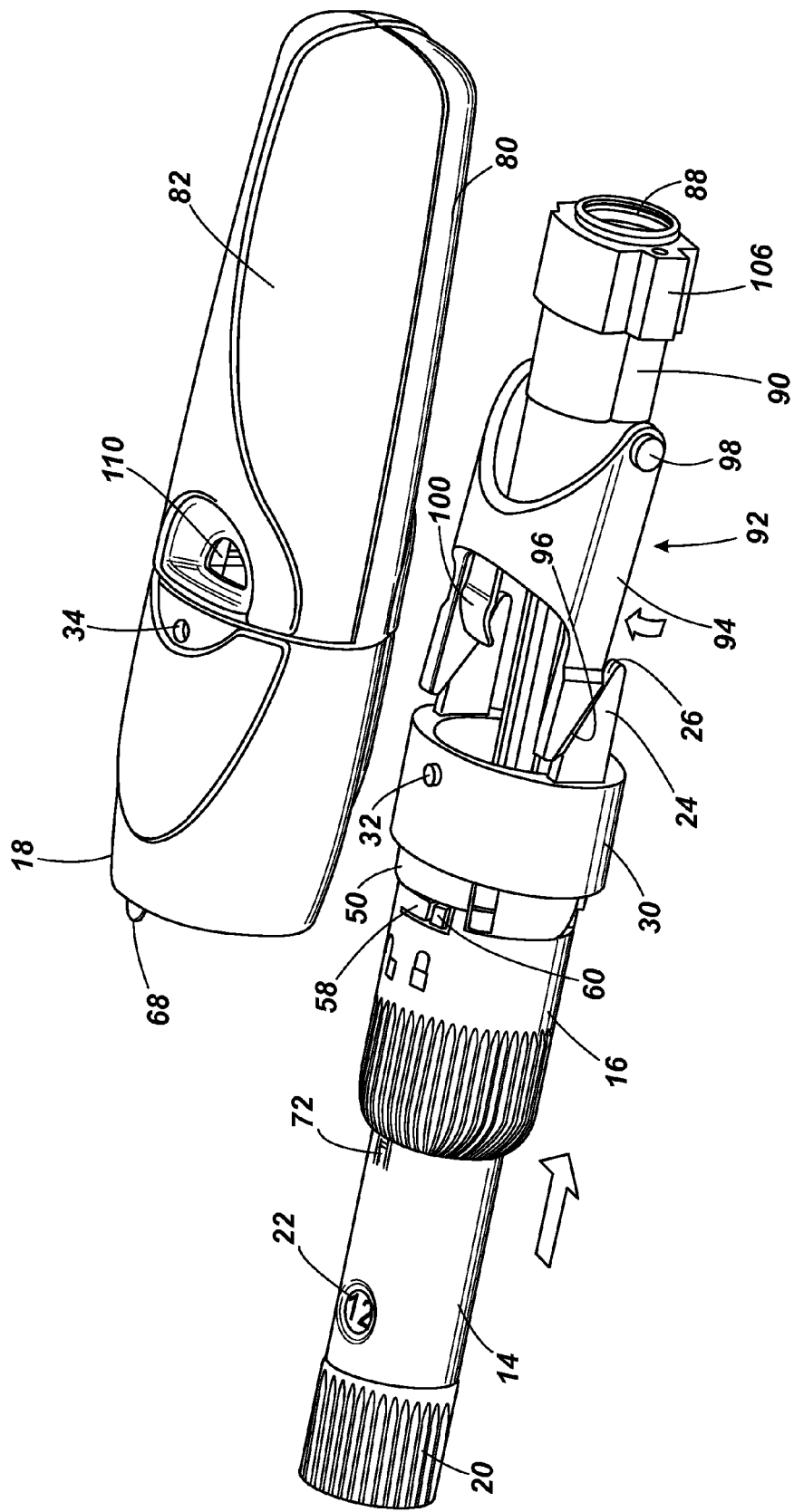
Figure 10A:
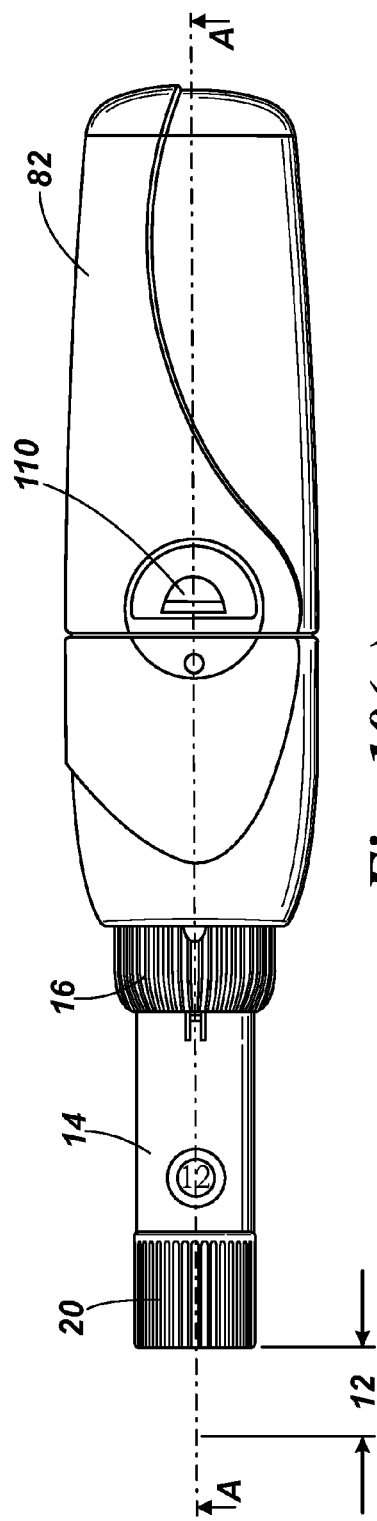
Figure 10B:
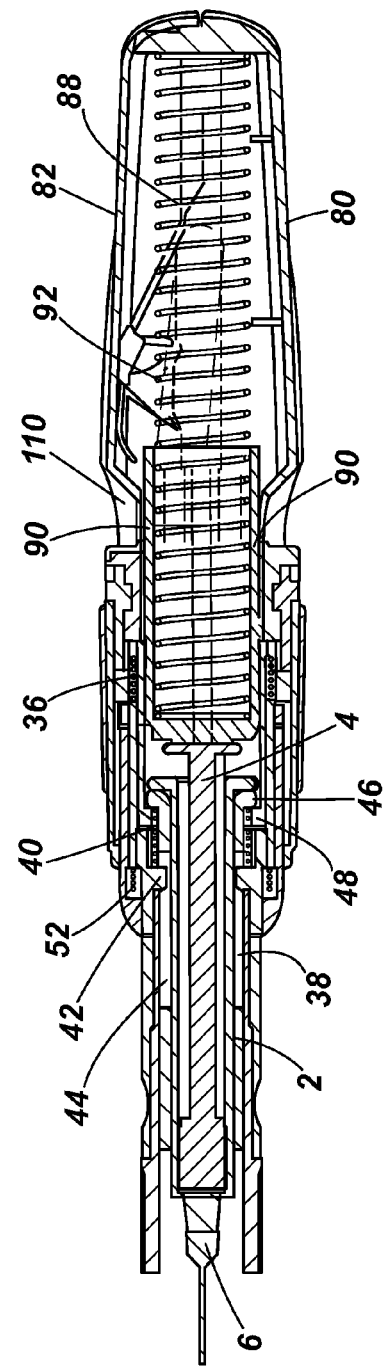
Figure 11A:
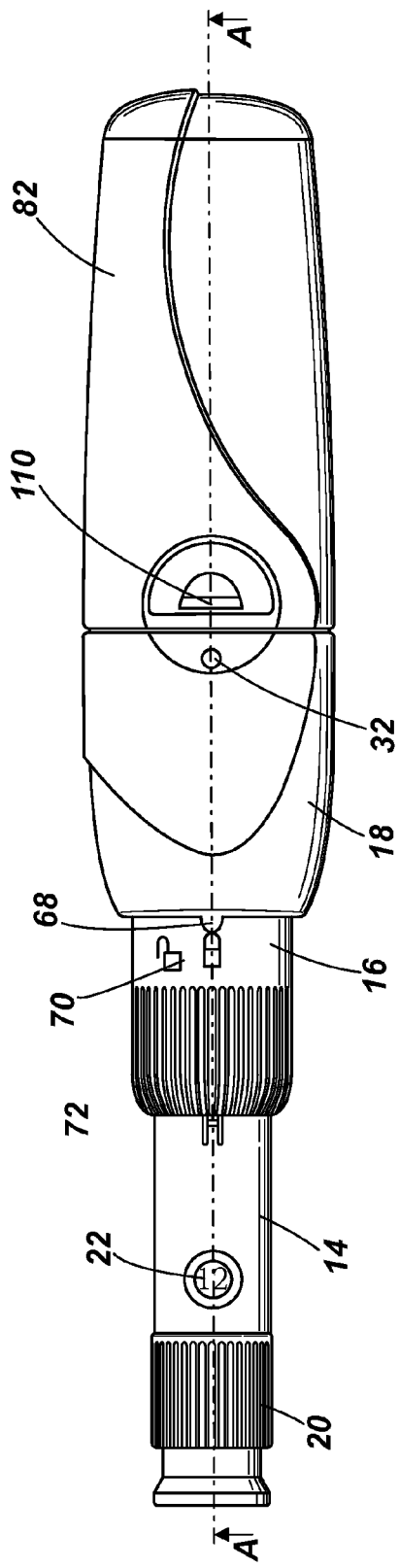
Figure 11B:
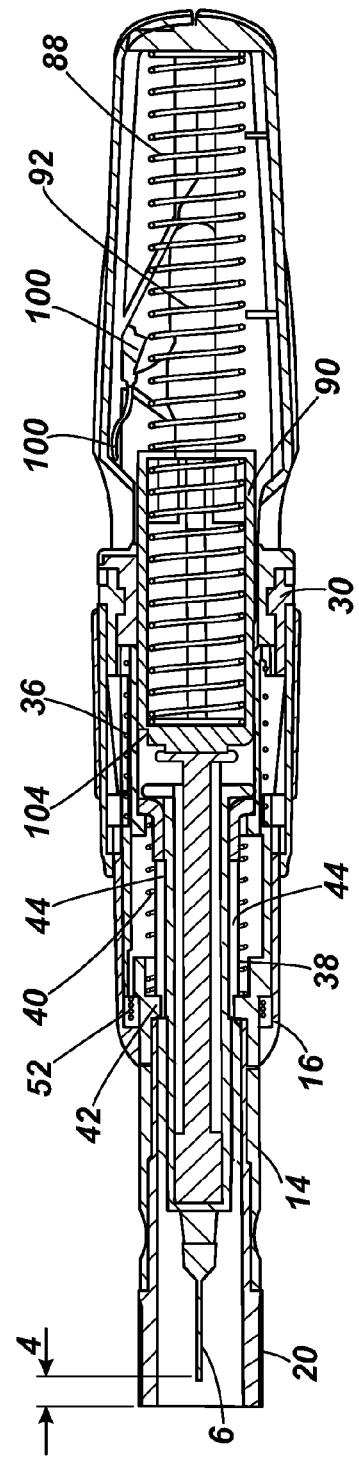

The autoinjector is then offered up to the injection site and pressed to cause the sleeve 14 and rotary dial 16 to move rearwardly into the housing. During the opening stages of this movement, the tooth 60 on the rotary dial 16 is shifted axially clear of the 'unlocked' recess so it is now free to rotate back part way towards axial alignment with the 'locked' recess by the influence of the torsion spring 52 (but shifted rearwardly). Angular movement of the sleeve 16 is restrained by the extension 50 engaging the web 66. Continued pressing drives the sleeve 14 and dial 16 further into the housing until the prongs 24 on the sleeve 14 engage the arms 94 on the latch, with the respective ramp surfaces 26 and 96 cooperating to cause the latch 92 to pivot against its spring bias 100 to release the piston 90 (see FIG. 9). The piston moves forwardly to engage the plunger 4 of the syringe. Initially, the liquid medicament inside the syringe barrel 2 acts as a solid so that the pressure on the syringe plunger moves the barrel 2 forwardly to cause the needle 6 to project from the sleeve 14 to penetrate the flesh of the user. Forward movement is of the syringe and the syringe carrier 38 is stopped when the out-turned end 46 of the syringe carrier engages the in-turned lip 48 on the collar 30. Thereafter the piston 90 continues to move forwardly moving the plunger 4 to expel a dose (see FIG. 10(*b*)). During this period the sleeve 14 has remained relatively stationary as the syringe carrier 38 moves forwardly to compress the spring 40, with the lugs 42 on the inside of the sleeve 14 running in slots 44 in the syringe carrier. The piston is now visible through the injection complete window 110.

Pulling the device away from the skin allows the sleeve 14 to move forwardly under the influence of springs 36 and 40 so that the sleeve 14 and the depth adjuster 20 form a needle shroud portion (15) to shroud the syringe needle 6. Just as the sleeve nears its forwardmost position, the extensions 50 slide forwardly off the ends of the web 66 of the front case 18, with the extensions then abutting the arms 24 of the sleeve 14 so that the extensions 50 are now in blocking alignment with the web 66 and the dial 16 returns to its locked position upon withdrawal, with the teeth 60 in the locked recess 62. The sleeve 14 and depth adjuster 20 are therefore locked against retraction movement and form a needle shroud portion (15) to shroud the needle, and the dial 16 is in its locked position.

The front and rear assemblies may then be separated to allow withdrawal of the syringe ready for the next cycle.

Figure 14:
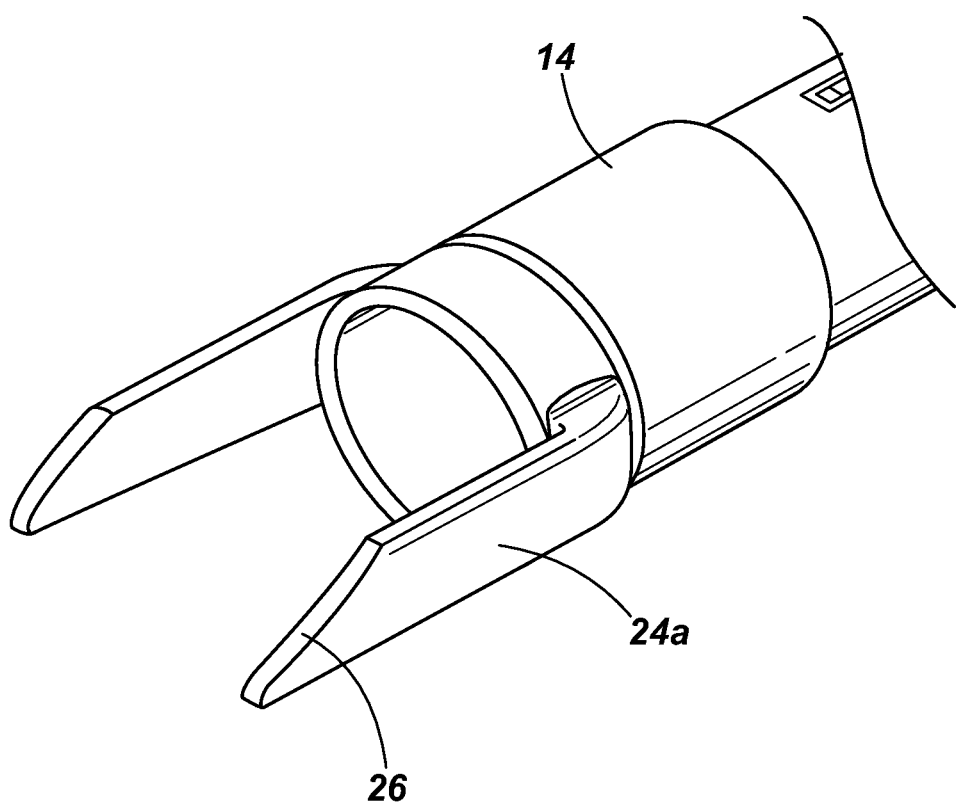
FIG. 14 is a detailed view of the rear end of the sleeve 14 in an alternative embodiment.

In the above embodiment, there are three main components in the locking function, i.e. the front cover, the dial and the sleeve. In a variant, (not illustrated), Instead of having the front cover and sleeve angularly fixed, with the dial being rotatable between locked and unlocked positions, in an alternative arrangement the dial is omitted and instead the sleeve is capable of limited rotation against a spring bias to lock/unlock and then reset with the respective locking abutments and recesses on the sleeve and body. Otherwise the embodiment operates generally as above. In this variant the sleeve 14 is provided with the extensions 50 and the teeth 60, and the sleeve is rotatably carried in the front housing. In FIG. 3, for example the sleeve 14 and dial 16 would be secured together or formed integrally, and the sleeve/dial are rotatable as one relative to the front housing. In this arrangement of course a suitably modified configuration is provided for utilising the rearward movement of the sleeve to unlatch the piston. In one arrangement, the prongs 24 extending from the rear of the sleeve 14 may be rotatably attached to the sleeve by a suitable arrangement that ensures that the prongs 24 move longitudinally with the sleeve but remain angularly fixed with respect to the housing when the sleeve 14 is rotated between locked and unlocked positions. For example, the prongs 24*a* may be formed on a cylindrical shell 24*b*, that is journalled on the rear of the sleeve as shown in FIG. 14.

The invention claimed is:

1. An autoinjection device, comprising:
   a main body adapted in use to receive a syringe configured for longitudinal movement with respect to said main body between a rearward and a forward position;
   a drive mechanism in said main body, the drive mechanism comprising a drive spring, a drive member longitudinally moveable within the main body, and a latch for latching the drive member in a primed position, the drive mechanism configured for being fired to drive said syringe forwardly relative to said main body to cause a needle at a forward end of said syringe to penetrate flesh of a user and inject a dose from said syringe in use;
   an actuating member comprising a needle shroud portion in a forward portion of said main body, the actuating member being operable to release said latch,
   the actuating member being moveable with respect to the main body from a first position in which the needle is shrouded by said needle shroud portion, to a second position in which said drive mechanism is fired,
   wherein upon completion of an injection from the syringe, return of the actuating member to its first position shrouds the needle with the needle shroud portion; and
   a locking member associated with said actuating member, the locking member configured for preventing said actuating member from reaching its second position when the locking member is in a locked position, the locking member and the actuating member being moveable relative to each other,
   wherein when the actuating member is in its first position, the locking member is moveable between its locked position in which the locking member prevents the actuating member from being moved, and an unlocked position in which the actuator member is free to move, and
   wherein on moving said locking member to its unlocked position, and after moving said actuating member to its second position, return of said actuating member to its first position is accompanied by return of said locking member to its locked position.

2. The autoinjection device according to claim 1, wherein said actuating member is biased towards its first position.

3. The autoinjection device according to claim 1, wherein said locking member is biased towards its locked position.

4. The autoinjection device according to claim 1, wherein said actuating member is linearly moveable between said first and second positions.

5. The autoinjection device according to claim 1, wherein said locking member and said main body have cooperating abutment surfaces that are rotated out of blocking alignment when said locking member is moved to the unlocked position.

6. The autoinjection device according to claim 1, wherein said latch comprises at least one side portion extending generally parallel to an axis of the drive spring and having an inclined surface adapted to cooperate with a respective complementary inclined surface on said actuating member to release said latch as said actuating member moves towards its second position.

7. The autoinjection device according to claim 1, wherein the main body is formed of separable forward and rearward parts, wherein said rearward part contains at least a major portion of said drive mechanism and said forward part supports said actuating member and said locking member.

8. The autoinjection device according to claim 1, wherein said actuating member extends forwardly of said main body.

9. The autoinjection device according to claim 1, wherein said actuating member includes a moveable adjustable portion associated therewith for adjusting an effective length of said actuating member.

10. The autoinjection device according to claim 1, wherein said actuating member is angularly moveable between its locked and unlocked positions when in said first position.

11. The autoinjection device according to claim 1, wherein said actuating member is manually moveable between its locked and unlocked positions when in said first position.

12. The autoinjection device according to claim 1, wherein said locking member comprises a locking element integrally formed with the actuating member, which cooperates with a respective locking element formed in a portion of the main body.

13. An autoinjection device, comprising:
a main body adapted in use to receive a syringe configured for longitudinal movement with respect to said main body between a rearward and a forward position;
a drive mechanism in said main body, the drive mechanism configured for being fired to drive said syringe forwardly relative to said main body to cause a needle at a forward end of said syringe to penetrate flesh of a user and inject a dose from said syringe in use;
an actuating member comprising a needle shroud portion in a forward portion of the main body, the actuating member being moveable with respect to the main body from a first position to a second position in which said drive mechanism is fired; and
a locking member associated with said actuating member, the locking member configured for preventing said actuating member from reaching its second position when the locking member is in a locked position, the locking member and the actuating member being moveable relative to each other between locked and unlocked positions when said actuating member is in the first position,
wherein on moving said locking member to its unlocked position, and after moving said actuating member to its second position, return of said actuating member to its first position is accompanied by return of said locking member to its locked position,
wherein upon completion of said injection, return of said actuating member to its first position shrouds the needle with said needle shroud portion, and
wherein said drive mechanism comprises a drive spring, a drive member longitudinally moveable within said main body, and a latch for latching the drive member in a primed position,
and wherein said actuating member is operable to release said latch.

14. The autoinjection device according to claim 13, wherein said latch comprises at least one side portion extending generally parallel to an axis of the drive spring and having an inclined surface adapted to cooperate with a respective complementary inclined surface on said actuating member to release the latch as the actuating member moves towards its second position.

15. The autoinjection device according to claim 13, wherein said locking member and said main body have cooperating abutment surfaces that are rotated out of blocking alignment when said locking member is moved to the unlocked position.

16. The autoinjection device according to claim 13, wherein the main body is formed of separable forward and rearward parts, wherein said rearward part contains at least a major portion of said drive mechanism and said forward part supports said actuating member and said locking member.

17. The autoinjection device according to claim 13, wherein said actuating member extends forwardly of said main body.

18. The autoinjection device according to claim 13, wherein said actuating member includes a moveable adjustable portion associated therewith for adjusting an effective length of said actuating member.

19. An autoinjection device, comprising:
a main body adapted in use to receive a syringe configured for longitudinal movement with respect to said main body between a rearward and a forward position;
a drive mechanism in said main body, the drive mechanism configured for being fired to drive said syringe forwardly relative to said main body to cause a needle at a forward end of said syringe to penetrate flesh of a user and inject a dose from said syringe in use;
an actuating member comprising a needle shroud portion in a forward portion of said main body, the actuating member being moveable with respect to the main body from a first position in which the needle is shrouded by said needle shroud portion, to a second position in which said drive mechanism is fired,
wherein upon completion of an injection from the syringe, return of the actuating member to its first position shrouds the needle with the needle shroud portion; and
a locking member associated with said actuating member, the locking member configured to have limited angular movement with respect to said actuating member but is longitudinally fixed with respect thereto, and the locking member configured for preventing said actuating member from reaching said second position when the locking member is in the locked position, the locking member and the actuating member being moveable relative to each other, the locking member being angularly moveable between a locked and unlooked position,
wherein when the actuating member is in its first position, the locking member is moveable between its locked position in which the locking member prevents the actuating member from being moved, and an unlocked position in which the actuator member is free to move,
wherein on moving said locking member to its unlocked position, and after moving said actuating member to its second position, return of said actuating member to its first position is accompanied by return of said locking member to its locked position,
wherein one of said actuating member and said locking member has spaced recesses provided therein, and the other of said actuating member and said locking member has a toothed element,
one of said spaced recesses in a locked position forming a locked recess and the other of said spaced recesses in an unlocked position forming an unlocked recess, wherein when the actuating member is in its first position, the one of said actuating member and said locking member having the toothed element is capable of angular movement such that the toothed element is moved from the locked recess to the unlocked recess, and wherein movement of the actuating member from its first position towards its second position acts to axially withdraw the toothed element from the unlocked recess whereupon the toothed element moves towards axial alignment with the locked recess.

20. The autoinjection device according to claim 19, wherein said locking member and said main body have cooperating abutment surfaces that are rotated out of blocking alignment when said locking member is moved to the unlocked position.

21. The autoinjection device according to claim 19, wherein the main body is formed of separable forward and rearward parts, wherein said rearward part contains at least a major portion of said drive mechanism and said forward part supports said actuating member and said locking member.

22. The autoinjection device according to claim 19, wherein said actuating member extends forwardly of said main body.

\* \* \* \* \*